US00RE44533E

(19) United States
(12) Reissued Patent
Timmins et al.

(10) Patent Number: US RE44,533 E
(45) Date of Reissued Patent: Oct. 8, 2013

(54) DIAGNOSIS OF INFECTION IN THE LUNGS OF PATIENTS

(75) Inventors: Graham Timmins, Albuquerque, NM (US); Vojo P. Deretic, Placitas, NM (US)

(73) Assignee: STC.UNM, Albuquerque, NM (US)

(21) Appl. No.: 13/467,514

(22) Filed: May 9, 2012

Related U.S. Patent Documents

Reissue of:
(64) Patent No.: 7,717,857
Issued: May 18, 2010
Appl. No.: 12/150,199
Filed: Apr. 25, 2008

U.S. Applications:
(63) Continuation of application No. PCT/US2008/005412, filed on Apr. 25, 2008.

(60) Provisional application No. 60/926,191, filed on Apr. 25, 2007, provisional application No. 60/927,670, filed on May 4, 2007, provisional application No. 60/958,615, filed on Jul. 6, 2007.

(51) Int. Cl.
*A61B 5/08* (2006.01)

(52) U.S. Cl.
USPC ..... 600/532; 600/529; 73/23.3

(58) Field of Classification Search
None
See application file for complete search history.

(56) References Cited

U.S. PATENT DOCUMENTS

| | | | |
|---|---|---|---|
| 5,093,255 | A | 3/1992 | Kakimoto et al. |
| 6,067,989 | A | 5/2000 | Katzman |
| 2003/0212004 | A1 | 11/2003 | Gaston et al. |
| 2007/0062255 | A1 | 3/2007 | Talton |

OTHER PUBLICATIONS

Deturk, W. E. The adaptive formation of crease by washed suspensions of *Pseudomonas aeruginosa*. J Bacteriol 70,187-91(1955).
Jahns, T. Regulation of urea uptake in *Pseudomonas aeruginosa*. Antonie Van Leeuwenhoek 62, 173-9 (1992).
Karmali, K., Karmali, A., Teixeira, A. & Curto, M. J. The use of Fourier transform infrared spectroscopy to assay for urease from *Pseudomonas aeruginosa* and *Canavalia ensiformis*. Anal Biochem 331,115-21(2004).
Sundstrom, J., Jacobson, K., Munck-Wikland, E. & Ringertz, S. *Pseudomonas aeruginosa* in otitis exteina. A particular variety of the bacteria? Arch Otolaryngol Head Neck Surg 122, 833-6 (1996).
Deretic, V. in Persistent Bacterial Infections (ed. Nataro, J. P., Blaser, M. J., Cunningham-Runddles, S.) 305-326 (ASM Press, Washington, DC, 2000).
Goldberg, J. B. & Pier, G. B. The role of the CFTR in susceptibility to *Pseudomonas aeruginosa* infections in cystic fibrosis. Trends in Microbiology 8, 514 20 (2000).
FitzSimmons, S. C. The changing epidemiology of cystic fibrosis. Journal of Pediatrics 122, 1-9 (1993).
Govan, J. R. W. & Deretic, V. Microbial pathogenesis in cystic fibrosis: mucoid *Pseudomonas aeruginosa* and *Burkholderia cepacia*. Microbiological Reviews 60, 539-574 (1996).
Martin, D. W. et al. Mechanism of conversion to mucoidy in *Pseudomonas aeruginosa* infecting cystic fibrosis patients. Proceedings of the National Academy of Sciences of the United States of America 90, 8377-8381 (1993).
Fyfe, J. A. & Govan, J. R. Alginate synthesis in mucoid *Pseudomonas aeruginosa*: a chromosomal-locus involved in control. Journal of General Microbiology 119, 443-50 (1980).
McAvoy, M. J. et al. Isolation of mucoid strains of *Pseudomonas aeruginosa* from non-cystic- fibrosis patients and characterisation of the structure of their secreted alginate. Journal of Medical Microbiology 28, 183-9 (1989).
Pedersen, S. 5.., Hoiby, N., Espersen, F. & Koch, C. Role of alginate in infection with mucoid *Pseudomonas aeruginosa* in cystic fibrosis. Thorax 47, 6-13 (1992).
Koch, C. & Hoiby, N. Pathogenesis of cystic fibrosis. Lancet 341, 1065-9 (1993).
Pedersen, S. S. Lung infection with alginate-producing, mucoid *Pseudomonas aeruginosa* in cystic fibrosis. APMIS 100(Suppl. 28), 1-79 (1992).
Firoved, A. M., Ornatowski, W. & Deretic, V. Microarray analysis reveals induction of lipoprotein genes in mucoid *Pseudomonas aeruginosa*: implications for inflammation in cystic fibrosis. Infection & Immunity 72, 5012-8 (2004).
Koch, C. Early infection and progression of cystic fibrosis lung disease. Pediatric Pulmonology 34, 232-6. (2002).
Bonfield, T. L. et al. Inflammatory cytokines in cystic fibrosis lungs. American Journal of Respiratory & Critical Care Medicine 152, 2111-2118 (1995).
Cobb, L. M., Mychaleckyj, J. C., Wozniak, D. J. & Lopez-Boado, Y. S. *Pseudomonas aeruginosa* flagellin and alginate elicit very distinct gene expression patterns in airway epithelial cells: implications for cystic fibrosis disease. J Immunol 173, 5 659-70 (2004).
Castric, P. A. Glycine metabolism by *Pseudomonas aeruginosa*: hydrogen cyanide biosynthesis. J Bacteriol 130, 826-31 (1977).
Castric, P. A. Hydrogen cyanide production by *Pseudomonas aeruginosa* at reduced oxygen levels. Can J Microbiol 29, 1344-9 (1983).
Firoved, A. M. & Deretic, V. Microarray analysis of global gene expression in mucoid *Pseudomonas aeruginosa*. J Bacteriol 185,1071-81(2003).
Gallagher, L. A. & Manoil, C. *Pseudomonas aeruginosa* PA01 kills *Caenorhabditis elegans* by cyanide poisoning. J Bacteriol 183, 6207-14 (2001).
Hojberg O. et al. Determination of 15N Abundance in Nanogram Pools of NO-3 and NO-2 by Denitrification Bioassay and Mass Spectrometry. Applied and Environmental Microbiology 60(7):2467-2472, Jul. 1994.*

(Continued)

*Primary Examiner* — Ralph Gitomer
(74) *Attorney, Agent, or Firm* — Henry D. Coleman; R. Neil Sudol

(57) ABSTRACT

The present invention relates to methods for detecting P aeruginosa infection and bacterial burden in the lungs of patients who are at risk for P. aeruginosa infections, especially including patients with Cystic Fibrosis (CF). The present method provides numerous tests (breath, blood, urine) which are readily administered to a patient that will sensitively and specifically detect the presence and extent of lung infection P. aeruginosa (both mucoid and non-mucoid), and allow monitoring of bacterial load as a parameter in monitoring treatment.

35 Claims, 3 Drawing Sheets

(56) References Cited

OTHER PUBLICATIONS

Carterson, et al., The Transcriptional Regulator AlgR Controls Cyanide Production in *Pseudomonas aeruginosa*. J. Bacteriol Oct. 2004, 186:6837-6844.

Ramsey, D. M. & Wozniak, D. J. Understanding the control of *Pseudomonas aeruginosa* alginate synthesis and the prospects for management of chronic infections in cystic fibrosis. Molecular Microbiology 56, 309-22 (2005).

* cited by examiner

DIAGNOSIS OF INFECTION IN THE LUNGS OF PATIENTS

Matter enclosed in heavy brackets [ ] appears in the original patent but forms no part of this reissue specification; matter printed in italics indicates the additions made by reissue.

This application is a continuation of PCT/US08/05412 dated Apr. 25, 2008, which claims benefit to 60/958,615 dated Jul. 6, 2007, which claims benefit to 60/927,670 dated May 4, 2007, which claims benefit to 60/926,191 dated Apr. 25, 2007.

The present application claims priority from U.S. provisional applications Ser. No. 60/926,191, filed Apr. 25, 2007, Ser. No. 60/927,670, filed May 4, 2007 and Ser. No. 60/958,615, filed Jul. 6, 2007, each of which applications is incorporated by reference herein in its entirety.

RELATED APPLICATIONS AND FEDERALLY SPONSORED RESEARCH

[The present invention was made with government support under Grant Nos. A1 050825 and AI 31139 awarded by the National Institutes of Health. Consequently, the Government retains rights in this invention.] *This invention was made with government support under grant numbers A1 050825 and A1 31139, awarded by the National Institutes of Health. The government has certain rights in the invention.*

FIELD OF THE INVENTION

The present invention relates to methods for detecting P aeruginosa infection and bacterial burden in the lungs of patients who are at risk for P. aeruginosa infections, especially including patients with Cystic Fibrosis (CF). The present method provides numerous tests (breath, blood, urine) which are readily administered to a patient that will sensitively and specifically detect the presence and extent of lung infection P. aeruginosa (both mucoid and non-mucoid), and allow monitoring of bacterial load as a parameter in monitoring treatment.

In addition, the present invention also relates to a method for detecting non-mucoid and mucoid P. aeruginosa infection and its burden in the lungs of patients with Cystic Fibrosis (CF), specifically to a method which is a special breath test that will sensitively and specifically detect the presence and extent of lung infection by non-mucoid and mucoid P. aeruginosa, and allow monitoring of mucoid bacterial load as a parameter in treatment. It is achieved by sensitive detection of volatile (or non-volatile) products of the denitrification pathway that occurs in P. aeruginosa. These can be detected either as isotopically labeled products from labeled precursors (such as $^{15}NO_3$ or $^{15}NO_2$).

BACKGROUND OF THE INVENTION

Cystic fibrosis is a major genetic disease in many populations, and has been transformed from a life ending, to a life-shortening disease through aggressive therapy especially that aimed at the major pathogen in CF P. aeruginosa. However, there is no currently available method to rapidly determine whether a CF patient is actively infected with P. aeruginosa or to assess whole-lung bacterial levels.

The progressive lung damage and deterioration of respiratory function in cystic fibrosis (CF) arises from a characteristic pattern of bacterial colonization of the lung, with chronic Pseudomonas aeruginosa infections being centrally important to the lung pathology and progressive tissue damage in CF patients. More than 80% of CF patients over 26 years old are chronically infected with P. aeruginosa, and these infections persist, despite aggressive antibiotic therapy. After initial infection with wild-type, non-mucoid strains, exemplified by strains such as PAO1, conversion of P. aeruginosa to the mucoid phenotype in the CF host occurs and increases bacterial resistance not only to host clearance and defense mechanisms, but also to antibiotic interventions. The mucoid phenotype is characterized by production of large amounts of the exopolysaccharide alginate. Mucoid conversion is concomitant with the establishment of chronic bacterial colonization and increases inflammation and lung damage, while causing pulmonary function to decline. Furthermore, alginate modulates host defenses to allow a persistent infection. Accordingly, mucoid conversion results in a poor prognosis for CF patients to heal Rapidly knowing if mucoid conversion has occurred, and the extent of mucoid pseudomonas burden would greatly improve therapies. However, there is no currently available method to rapidly determine whether a CF patient is infected, or colonized with mucoid R aeruginosa or to assess whole-lung mucoid bacterial levels. Currently, culture of sputum samples, or bronchioalveolar lavage, together with phenotypic (and genotypic) analysis. We propose a novel detection system that will revolutionize mucoid bacterial detection, and so management of CF. By making key modifications to current H pylori breath test, we will furnish a specific and selective test for the presence and bacterial load of mucoid P aeruginosa in CF lungs.

An H. pylori breath test is presently available for detecting H. pylori levels in the gut of patient. The basis for the H pylori breath test is that a drink containing labeled urea (carbon-13 or carbon-14) is ingested, with the urea rapidly encountering urease-positive H. pylori bacteria in the gut (if the bacteria is present) that break down the urea into labeled $CO_2$ that is detected in the breath about 15 minutes afterwards.

P. aeruginosa also expresses urease[1-4], has the urease ureaureG gene cluster whose expression is modifiable (Deretic & Timmins, unpublished microarray data), and consequently, is susceptible to detection by breath tests if the appropriate technology is developed and applied. Because P. aeruginosa is so exquisitely associated with the CF lung, and not the normal population, by targeting the CF patient, high specificity can be achieved.

SUMMARY

The present invention provides a method for detecting mucoid and non-mucoid P. aeruginosa in a patient with cystic fibrosis (CF), wherein an isotopically labeled compound such as a nitrate salt, a nitrite salt, nitric oxide (NO) donor, glycine and/or urea is delivered to the patient, either orally, via an intravenous route or preferably, directly to the lungs of the CF patient in an inhaled dosage form. In the presence of P. aeruginosa, the labeled compounds are converted to labeled nitrate, nitrate, nitric oxide, nitrogen, nitrous oxide, cyanate, thiocyanate, hydrogen cyanide (HCN), carbon dioxide ($CO_2$) which is detected upon exhalation or in the blood, serum, plasma or urine of the patient or subject. The amount of conversion can be used as an assay of overall bacterial load, response to treatments, and other important parameters to the management of CF, including the extent to which non-mucoid bacteria have been converted to the more potent and dangerous mucoid bacteria.

The present invention relates to a method for identifying the existence of a P. aeruginosa infection in the lungs of a subject (CF patient) to be diagnosed and whether the infection has advanced to a more problematic mucoid stage from a non-mucoid stage.

According to the present invention there is provided a method for the diagnosis of Psedomonas aeruginosa in the lungs of a CF patient or subject, including the steps of:

(i) administering at least one isotopically labeled compound selected from the group consisting of a pharmaceutically acceptable nitrate salt, a pharmaceutically acceptable nitrite salt, NO gas, a nitric oxide (NO) donor/precursor such as a pharmaceutically acceptable S-nitrosothiol compound (e.g., an alkylthionitrile, S-glutathione, S-nitroso-N-acetylpenicillamine), urea and/or glycine (isotopically labeled metabolic precursors referred to in context collectively as "active agents", "active compounds" "isotopically labeled active agents or compounds") to said patient such that, if the patient has a P. aeruginosa infection in the lungs of the subject, the said isotopically labeled compound is metabolized to at least one isotopically labeled metabolite (preferably, a gas) selected from the group consisting of nitrate, cyanate, thiocyanate (for detection in urine), or $N_2$, NO, $N_2O$, $CO_2$ and HCN (for detection in the breath of the subject) and (ii) the metabolite produced in step (i) is quantified, such that the amount of isotopically labeled metabolite is evidence of a P. aeruginosa infection. A positive reading of any of the isotopically labeled metabolites may indicate the presence of a P. aeruginosa infection in the lungs of the subject and a high positive reading of HCN, cyanate or thiocyanate relative to other metabolites identified and quantified will support the likelihood that the P. aeruginosa infection contains significant mucoid P. aeruginosa.

In the present invention the metabolites are measured in the urine of the subject or by analyzing a plurality of exhaled breaths of the subject to determine a concentration of said metabolic/cleavage product(s), the concentration indicating the presence or absence of P. aeruginosa and high levels of glycine metabolites (cyanate, thiocyanate in urine or HCN in breath) compared to a control, evidencing the presence of mucoid P. aeruginosa. Optional steps include fitting the concentrations to a curve; and analyzing the curve or plateau to determine the extent of infection.

Preferably, the metabolite obtained above is determined by analyzing exhaled breath of the subject. Analyzing the exhaled breath of the subject is repeated substantially at a particular time or times until a predetermined time period (which can range from as little as several breaths in a short period to a number of breaths in several minutes or more) has elapsed. This can be done by collecting breaths from a subject over a predetermined period of time or times. The predetermined period of time may be determined by analyzing the activity of control subjects with P. aeruginosa infections to cleave/metabolize isotopically labeled nitrate, nitrite, S-nitrosothiol compound, urea and/or glycine measuring the concentration of isotopically labeled nitrogen, nitric oxide (NO), nitrous oxide ($N_2O$), carbon dioxide and/or hydrogen cyanide which is found in the exhaled breath of the control subjects as a function of time after administration of the metabolic precursor.

The urine or exhaled breath of the subject is analyzed for content of the isotopically labeled element which evidences the residence of P. aeruginosa. In certain embodiments related to a breath analysis, the step of analyzing the exhaled breath of the subject is repeated substantially until a particular accuracy for analyzing the data is reached. In certain preferred aspects of the invention, a ratio of the concentration of an isotopically labeled element to a non-isotopically labeled element measured for a sample taken at one or more predetermined times and for one or more predetermined periods is calculated and a graph of the ratio (y-axis) as a function of time (x-axis) is provided. Preferably, the breath of the subject is analyzed by an infrared laser spectrometer or a mass spectrometer to determine concentrations of isotopically labeled elements and non-isotopically labeled elements. In a particularly preferred clinical diagnostic embodiment, a breath test according to the present invention will be designed to determine the existence of P. aeruginosa and in particular, mucoid P. aeruginosa, in the lungs of a CF patient or subject.

According to further preferred embodiments of the present invention, the nitrate, nitrite, NO gas, or S-nitrosothiol (stable NO precursor compound) urea and glycine are all isotopically-labelled. In the case of isotopically labeled nitrate, nitrite or the S-nitrosothiol compound, each of these compounds is labeled with an isotopically labeled nitrogen (nitrogen-15) or oxygen (oxygen-17, oxygen-18), preferably labeled Nitrogen, and if P. aeruginosa is present in the lungs of a subject, the cleavage/metabolic product is an isotopically labeled (nitrogen-15) gas such as $N_2$, or an isotopically labeled (nitrogen-15) or (oxygen-17, oxygen-18) gas in the case of $N_2O$ or NO (note that a nitrogen-15 labeled gas is preferred), which may be measured/analyzed in the breath of the subject. In the case of urea, this may be isotopically labeled with nitrogen-15, carbon-13, oxygen-17 or oxygen-18, preferably with nitrogen-15 and/or carbon-13, such that if P. aeruginosa is present in the lungs of the subjected to be tested, the urea will be cleaved/metabolized to isotopically labeled ammonia and/or carbon dioxide. Using isotopically labeled urea (labeled accordingly), the resulting ammonia is nitrogen-15 labeled, whereas the carbon dioxide is carbon-13 labeled and/or oxygen-17 and/or oxygen-18 labeled. In the case of glycine, the glycine is labeled with nitrogen-15 or carbon-13 or mixtures thereof, such that the resulting HCN gas, cyanate or thiocyanate (urine analysis) is isotopically labeled with nitrogen-15, carbon-13 or mixtures thereof. It is noted that although it is preferable to analyze for isotopically labeled (gaseous) nitric oxide/nitrous oxide/Nitrogen oxide/Nitrogen (nitrate, nitrite, NO precursor cleavage products/metabolites) and/or carbon dioxide (urea cleavage products/metabolites) and/or hydrogen cyanide (HCN) in the breath of a subject, it is also possible to analyze for isotopically labeled nitrite, nitrate, cyanate or thiocyanate or even dissolved $CO_2$/bicarbonate in the blood (plasma, serum) or urine of a subject as alternative cleavage products.

It is noted that in the case of the use of isotopically labeled urea, urea may be labeled with isotopically labeled carbon-13, nitrogen-15, oxygen-17 and/or oxygen 18, wherein the cleavage products to be analyzed from urea being acted upon by P. aeruginosa urease are isotopically labeled carbon dioxide and/or ammonia. In the case of isotopically labeled glycine, the glycine may be labeled with isotopically labeled carbon-13, nitrogen-15 or mixtures thereof wherein the cleavage products to be analyzed from glycine being acted upon by the cyanide synthase pathway in P. aeruginosa to form hydrogen cyanide gas (to be analyzed by breath analysis) and/or cyanate and/or thiocyanate anion (to be analyzed by blood/serum/plasma or urinalysis).

The present invention also relates to pharmaceutical compositions comprising effective amounts of nitrate salts (sodium or potassium), nitrite (sodium or potassium), S-nitrosothiol compound (e.g., an alkylthionitrile, S-glutathione, S-nitroso-N-acetylpenicillamine), urea and/or glycine in pulmonary dosage form. A preferred compound comprises an effective amount of glycine or a pharmaceutically acceptable salt thereof, preferably glycine and urea or pharmaceutically salts thereof, and more preferably a nitrate salt, a nitrite salt and/or an S-nitrosothiol compound in combination with the glycine and urea (or pharmaceutical salts thereof). This composition comprises these components in effective amounts, in combination with a pharmaceutically acceptable carrier, additive or excipient, as well as a propellant and optionally, a solvent and/or a dispersant. The composition, in its most preferred form, is adapted for pulmonary administration to the lungs of a subject or patient.

The present invention also relates to a composition in oral dosage form comprising effective amounts of at least one compound selected from the group consisting of a nitrate salt, nitrite salt, an NO precursor compounds such as an S-nitrosothiol compound (e.g., an alkylthionitrile, S-glutathione, S-nitroso-N-acetylpenicillamine) and mixtures thereof, in combination with an effective amount of urea and glycine (or a pharmaceutically acceptable salt thereof), all isotopically labeled, optionally in combination with a pharmaceutically acceptable carrier, additive or excipient and further optionally in combination with an effective amount of a urease inhibitor. The urease inhibitor is preferably included in oral dosage forms in order to inhibit the urease of H. pylori which may reside in the stomach/gastrointestinal tract of a subject and which can reduce and/or negate the effects of urea in helping to diagnose a P. aeruginosa infection in the lungs of a patient.

In another aspect of the invention, a kit for diagnosing P. aeruginosa in a subject or patient comprises a composition comprising at least one compound selected from the group consisting of a nitrate salt, nitrite salt, a NO precursor compound such as a S-nitrosothiol compound (e.g., an alkylthionitrile, S-glutathione, S-nitroso-N-acetylpenicillamine) and mixtures thereof, in combination with an effective amount of urea and glycine (or a pharmaceutically acceptable salt thereof), all isotopically labeled, optionally in combination with a pharmaceutically acceptable carrier, additive or excipient and further optionally in combination with an effective amount of a urease inhibitor and mixtures thereof in oral or pulmonary dosage form, a collection bag or vial to collect exhaled breaths from said subject or patient; and an optional instruction manual. In preferred aspects, the composition will comprise a combination of at least one compound selected from the group consisting of a nitrate salt, nitrite salt, an S-nitrosothiol compound (e.g., an alkylthionitrile, S-glutathione, S-nitroso-N-acetylpenicillamine) in combination with an effective amount of urea and glycine (or a pharmaceutically acceptable salt thereof), all isotopically labeled in pulmonary dosage form. In oral dosage form, such a combination of agents is combined with an optional effective amount of a urease inhibitor as otherwise disclosed herein.

DETAILED DESCRIPTION OF THE INVENTION

Figure 1:
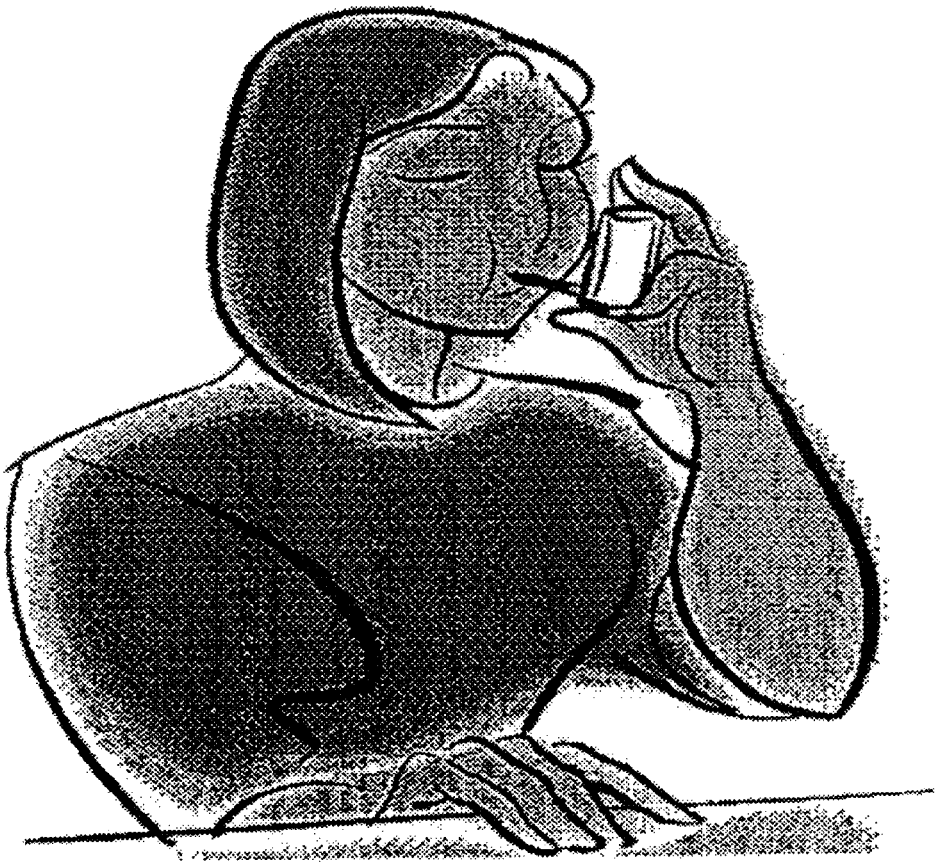
FIG. 1 shows a diagram representing how isotopically labeled compounds may be delivered to the lungs of a patient.
Figure 2:
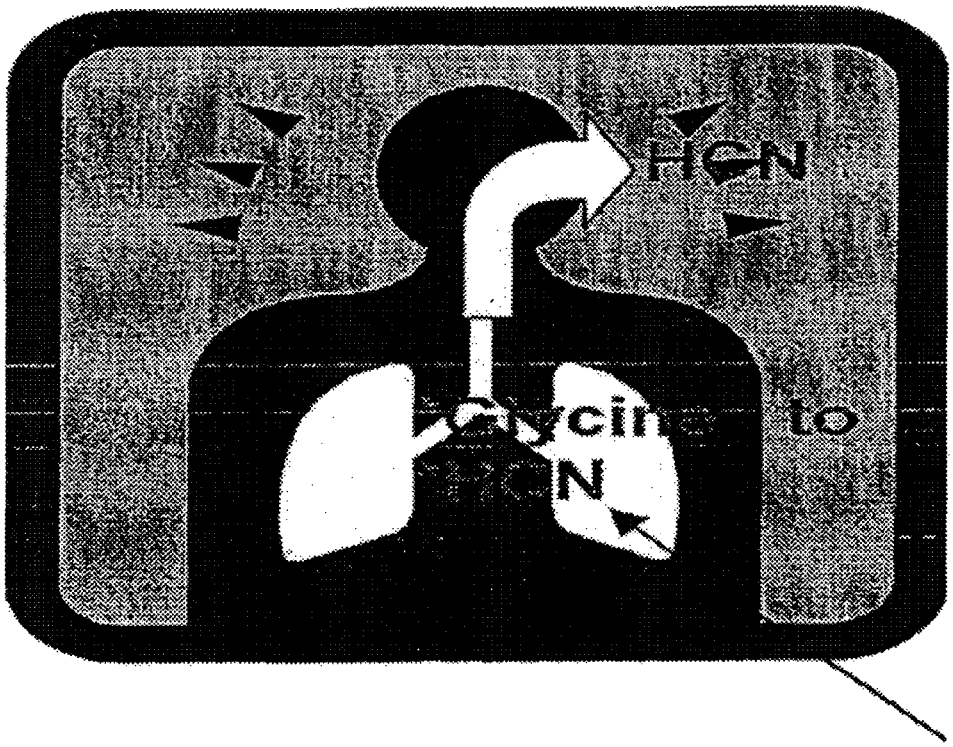
FIG. 2 shows a diagram representing how P. aeruginosa converts labeled glycine or urea to labeled HCN in the lung. Detection of labeled HCN indicates mucoid P. aeruginosa levels.
Figure 3:
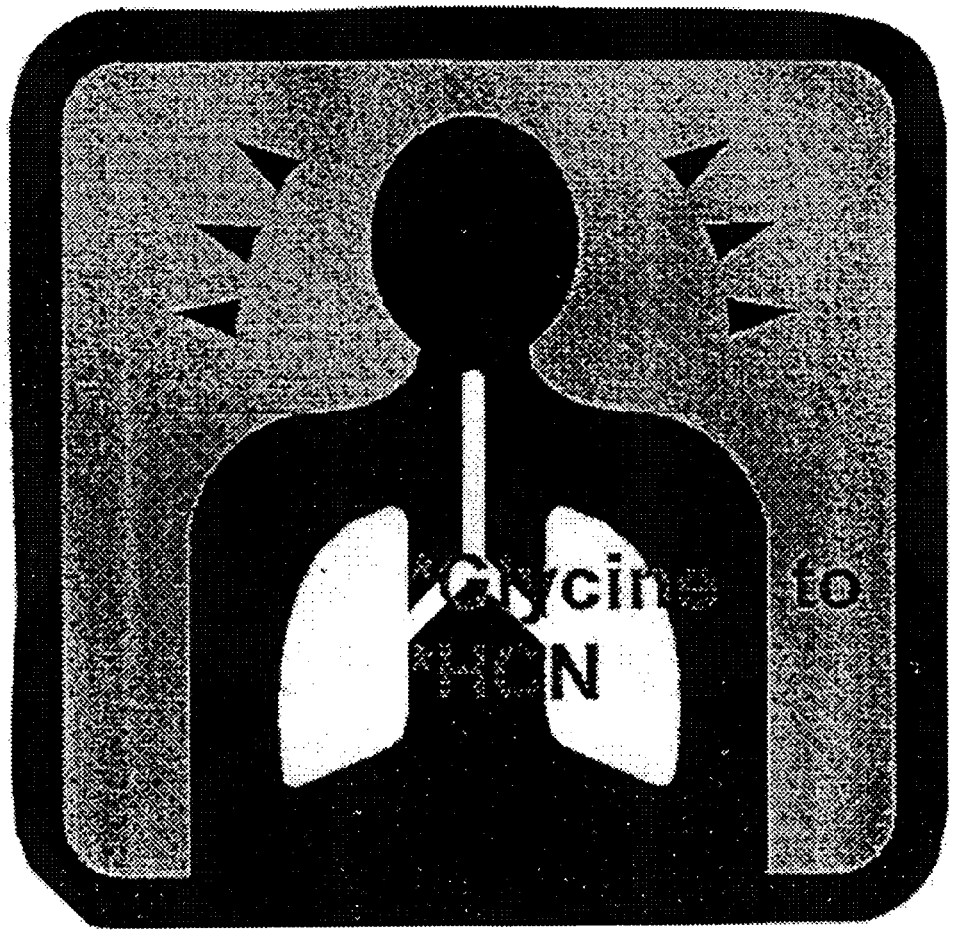
FIG. 3. shows a diagram representing how mucoid P. aeruginosa converts labeled glycine to labeled cyanate. Detection of labeled cyanate, or its metabolites such as thiocyanate, in the blood or urine at significant levels indicate the existence of significant levels of mucoid P. aeruginosa.

The following terms shall be used to describe the present invention. In instances where a term is not defined specifically, that term shall be accorded the ordinary meaning ascribed to the term by those of ordinary skill in the art when used within context.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an isotopically labeled element" includes a plurality (for example, two or more elements) of such elements, and so forth. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The term "patient" or "subject" is used to describe an individual subject or patient, a mammal, generally a human, who is at risk for developing a P. aeruginosa infection, in particular patients with cystic fibrosis. In the present invention, the term patient or subject generally refers to a patient or subject who has cystic fibrosis or is at least suspected of having cystic fibrosis.

The term "active agents", "active compounds" "isotopically labeled active agents or compounds" describes, within context, isotopically labeled metabolic precursors which are acted on by enzyme pathways of P. aeruginosa to produce identifiable and distinguishable metabolites which can be analyzed using conventionally available analytic tools and methodologies. Active agents according to the present invention include pharmaceutically acceptable nitrate salts (sodium and/or potassium), pharmaceutically acceptable nitrite salts (sodium and/or potassium), NO gas, a nitric oxide (NO) donor/precursor compound such as a pharmaceutically acceptable S-nitrosothiol compound (e.g., an alkylthionitrile, S-glutathione, S-nitroso-N-acetylpenicillamine), urea and/or glycine or pharmaceutically acceptable salts thereof. In the present invention, if a CF patient has a P. aeruginosa infection in his or her lungs, the isotopically labeled compound, which is delivered to the lungs and is metabolized to at least one isotopically labeled metabolite (preferably, a gas) selected from the group consisting of nitrate, nitrite, dissolved NO, cyanate, thiocyanate, bicarbonate/carbonate (for detection in blood, serum, plasma or urine), or $N_2$, NO, $N_2O$, $CO_2$ and HCN (for detection in the breath of the subject).

The terms "cleavage products" and "metabolites" are used in the specification synonymously to refer to isotopically labeled compounds that are formed by the action of P. aeruginosa on isotopically labeled active agents or active compounds as otherwise described herein.

The term "effective" refers to an amount of an active agent or compound (i.e., isotopically labeled nitrate, nitrite, NO gas, NO precursor compound (an S-nitrosothiol compound, e.g., an alkylthionitrile, S-glutathione, S-nitroso-N-acetylpenicillamine), urea and/or glycine) which is sufficient to produce a detectable level of a cleavage product or products, without an untoward level of adverse side effects, such as toxicity, irritation, allergy or hypersensitivity responses in a patient. The level of any such side effects should be commensurate with acceptable risk/benefit ratios. In the present invention, the term effective is used to describe an amount of a substrate or other substance or component which is used to effect an intended result within the context of its use.

The term "cystic fibrosis" or "CF" is used to describe one of the most common grave genetic (inherited) diseases. CF affects the exocrine glands and is characterized by the production of abnormal secretions, leading to mucous build-up. It is also characterized by severe respiratory problems including chronic infections of the lungs (P. aeruginosa), emphysema and progressive respiratory insufficiency. Chronic P. aeruginosa infection often results in accumulation of mucus in the lungs as the infection progresses from a non-mucoid to a mucoid phase. P. aeruginosa also expresses the enzyme cyanide synthase, from the cyanide synthase gene cluster (hcnA-C) that oxidizes glycine to hydrogen cyanide, and the expression of this enzyme is vastly upregulated in mucoid as opposed to non-mucoid P. aeruginosa. In addition to causing damage in the lungs, the accumulation of mucus can impair the pancreas and, secondarily, the intestine. Mucous build-up in lungs tends progressively to impair respiration. Without treatment, CF results in death for 95% of affected children before age 5.

With diligent medical care, patients with CF are surviving even beyond middle age. Early diagnosis of CF is of great importance. Early and continuing treatment of CF is essential for long-term survival. However, as more people with CF survive childhood, new problems are emerging, including urine leakage, which occurs most severely when their chest disease is most severe.

CF is inherited in an autosomal recessive manner and affects both boys and girls. One in 400 caucasian couples is at risk for having children with CF and their risk with each pregnancy is 1 in 4, with an overall risk that their child will have CF is 1 in 1600. The treatment of CF includes physical therapy to loosen the mucus in the lungs, pancreatic enzymes, and medications to fight dangerous infections of the lungs. CF is caused by mutation in the gene encoding CFTR (cystic fibrosis conductance regulator) on chromosome 7. The most common mutation, DeltaF508, results in the production of a misfolded CFTR protein that is retained in the endoplasmic reticulum and targeted for degradation.

The term "Pseudomonas aeruginosa" or P. aeruginosa is used to describe a g, aerobic, rod-shaped bacterium with unipolar motility, which commonly resides in the lungs (and other tissue) of patients with cystic fibrosis. An opportunistic human pathogen, P. aeruginosa is also an opportunistic pathogen of plants. P. aeruginosa is the type species of the genus Pseudomonas.

P. aeruginosa secretes a variety of pigments, including pyocyanin (blue-green), fluorescein (yellow-green and fluorescent, now also known as pyoverdin), and pyorubin (red-brown). P. aeruginosa is often preliminarily identified by its pearlescent appearance and grape-like odor in vitro. In the past, definitive clinical identification of P. aeruginosa often includes identifying the production of both pyocyanin and fluorescein as well as its ability to grow at 42° C. Although classified as an aerobic organism, P. aeruginosa is considered by many as a facultative anaerobe as it is well adapted to proliferate in conditions of partial or total oxygen depletion. This organism can achieve anaerobic growth with nitrate as a terminal electron acceptor, and in its absence it is also able to ferment arginine by substrate-level phosphorylation. Adaptation to microaerobic or anaerobic environments is essential for certain lifestyles of P. aeruginosa, like during lung infection in cystic fibrosis patients where thick layers of alginate surrounding bacterial mucoid cells can limit the diffusion of oxygen.

The term "coadministration" is used to describe the administration of at least two active (isotopically labeled) compounds, in this case at least urea and glycine, and preferably urea and glycine in combination with at least one further compound selected from a nitrate salt, a nitrite salt, NO gas or a NO stable compound such as an S-nitrosothiol compound (e.g., an alkylthionitrile, S-glutathione, S-nitroso-N-acetylpenicillamine), all in effective amounts. Although the term coadministration preferably includes the administration of at least two active compounds to the patient at the same time, it is not necessary that the compounds actually be administered at the exact same time, only that amounts of compound will be administered to a patient or subject such that effective concentrations are found in the blood, serum or plasma, or in the pulmonary tissue at the same time.

The term "cleaves", "cleavage product" or "metabolite" is used with reference to the fact that an enzyme of P. aeruginoa can break down or metabolize at least one chemical bond of the active isotopically labeled compounds, forming "cleavage products" (e.g, nitrate, nitrite, nitric oxide, nitrous oxide, nitrogen gas, carbon dioxide, ammonia, hydrogen cyanide, cyanate or thiocyanate, etc), by chemical processes including, but not limited to, hydrolysis, oxidation/reduction and/or denitrification. In the present invention, the concentration of the cleavage product or products (in the breath, whole blood, serum, plasma or urine of a subject or patient) indicates the level of activity of P. aeruginosa species in the lungs (or other tissues) of the subject, which can be used to determine a diagnosis of infection by P. aeruginosa, and the intensity of the infection. A positive diagnosis indicates that P. aeruginosa is present in the lungs (or other tissues) of the subject and can indicate whether a P. aeruginosa infection is primarily a mucoid infection, which is a particularly dangerous infection for CF patients. In preferred aspects of the invention, the method for diagnosis is preferably a "breath test", due to its ease of use by analyzing the breath of the subject for evidence of cleavage product.

Examples of appropriate labels for the substrate, and hence for the cleavage product or products, are those which can be detected by an appropriate measuring instrument, conventional spectroscopic including UV and IR, mass spectroscopic, radiochemical techniques, electrochemical analysis (nitrates and nitrites in serum, blood and urine), laser spectroscopy, GC/mass spectroscopy, but which are substantially not harmful or toxic to the subject including, but not limited to, carbon-13 or carbon-14, oxygen-17, oxygen-18 or nitrogen-15, isotope-labeling. An isotope is a form of an element, such as carbon, with a specific mass. For example, carbon-12 has a mass of 12 atomic mass units. The term "isotope-labeling" means that the naturally more abundant isotope of each of these elements is at least partially replaced by a less abundant isotope. For example, the naturally more abundant carbon-12 atoms could be at least partially replaced by the less abundant carbon-13 atoms, permitting the cleavage product or products which carry the label to be more easily detected, since the less abundant isotope can be distinguished from the naturally more abundant isotope. Furthermore, the advantage of certain isotopes such as carbon-13 is that they are stable, so that they are not radioactive, unlike isotopes such as carbon-14. Note that carbon 14 may be used in rare instances in an animal experimentation setting, but is inappropriate for use in a therapeutic setting. Therefore, preferably stable, non-radioactive isotopes such as carbon-13 are used as labels in the present invention.

The term "isotopically labeled" shall mean isotopically labeled with carbon-13, nitrogen-15, oxygen-17 or oxygen-18 at positions on the which give rise to isotopically labeled cleavage products as otherwise disclosed herein after exposure to P. aeruginosa denitrification pathway (nitrates, nitrites, nitric oxide precursors), urease (urea), and cyanide synthase (glycine), respectively.

The term "radiometric" or "radioactive ratio" is used to describe a ratio of isotopically labeled hydrogen cyanide, cyanate or thiocyanate which is analyzed in a CF patient having a P. aeruginosa infection which is principally a mucoid producing infection compared to an infection in a CF patient which is principally a non-mucoid producing infection. Because mucoid P. aeruginosa expresses cyanide synthase to a far greater extent than does non-mucoid P. aeruginosa, this difference may be utilized to establish that a P. aeruginosa infection is a mucoid producing infection. By comparing concentrations of isotopically labeled HCN in the breath of CF patients tested using the methods of present invention, or cyanate or isocyanate levels in the blood, serum or urine of the tested CF patients with controls established for these same cleavage products for patients 1) without P. aeruginosa infection or 2) with a non-mucoid P. aeruginosa infection, one may readily assess the likelihood that the test patient has a mucoid P. aeruginosa infection based upon the results obtained. In the present invention, a radioactive ratio of the test patient of at least about 1.25 times, at least about 1.3, at least about 1.4, at least about 1.5, at least about 1.65, at least about 1.75, at least about 1.85, at least about 2.0, at least about 2.1, at least about 2.25, at least about 2.5, at least about 3.0, at least about 5.0 evidences the existence of a more severe mucoid P. aeruginosa infection in the lungs of the CF patient tested.

According to the present invention there is provided a method for the diagnosis of Psedomonas aeruginosa in the lungs of a CF patient or subject, including the steps of:

(a) administering at least one isotopically labeled compound selected from the group consisting of a pharmaceutically acceptable nitrate salt (e.g., sodium, potassium), a pharmaceutically acceptable nitrite salt (sodium potassium), NO gas, a NO (nitric oxide) precursor such as an S-nitrosothiol (e.g., an alkylthionitrile, S-glutathione, S-nitroso-N-acetylpenicillamine), urea and/or glycine to said patient such that, if the patient has a P. aeruginosa infection in the lungs of the subject, the said isotopically labeled compound is metabolized to at least one isotopically labeled cleavage product selected from the group consisting of nitrate, nitrite, $N_2$, NO, $N_2O$, $CO_2$, HCN, cyanate or thiocyanate and quantified. A positive reading of any of the cleavage products may indicate the presence of a P. aeruginosa infection and a high positive reading of HCN, cyanate or thiocyanate compared to a control value will support the likelihood of a mucoid P. aeruginosa infection in the patient's lungs. Once an infection is established, appropriate therapy (antibiotic therapy) and/or remediation may begin.

In preferred aspects of the invention, the isotopically labeled compound is a mixture of an effective amount of urea and glycine, and optionally at least one additional isotopically labeled compound selected from the group consisting of a nitrate salt, nitrite salt and a NO precursor in pulmonary dosage form for administration to the lungs of the CF patient to be tested and the cleavage products are gases (e.g., NO, $N_2O$, $N_2$, $CO/CO_2$, HCN) which are measured/analyzed for in the breath (a plurality of breaths) of the patient, the concentration of isotopically labeled gas indicating the presence or absence of a P. aeruginosa bacterial infection and the concentration of HCN indicating the presence or absence of a significant mucoid P. aeruginosa infection in the lungs of the CF patient tested. Optional steps include fitting the concentrations to a curve; and analyzing the curve or plateau to determine the extent of infection.

The present invention is a diagnostic test, preferably a breath test, which can be used to rapidly and accurately detect the presence of P. aeruginosa, and in certain preferred aspects, mucoid P. aeruginosa in the lungs of a CF patient or subject. Specifically, the present invention can be used to diagnose the presence of P. aeruginosa by the administration (preferably pulmonary/intratracheal administration) of a safe and effective amount of isotopically labeled nitrate salt (e.g., sodium, potassium), nitrite salt (sodium potassium), a NO (nitric oxide) precursor such as an S-nitrosothiol (e.g., an alkylthionitrile, S-glutathione, S-nitroso-N-acetylpenicillamine), urea and/or glycine to a subject and then detecting the concentration of at least one of the cleavage/metabolic products of these compounds preferably as gases in breath exhaled by the subject.

In preferred aspects of the invention, several breaths taken at a predetermined time after administration of one or more of these products (preferably urea and glycine and optionally, at least one compound selected from a nitrate salt, a nitrite salt or a NO precursor compound) is sufficient for providing a measure of isotopically labeled Nitrogen, carbon or oxygen. If the ratio of measured isotopically labeled element to non-isotopically labeled element is greater than a predetermined value, the existence and in many cases the severity of the P. aeruginosa infection may be readily determined. In addition, if a concentration of HCN is determined to be greater than a predetermined value or ratio, the existence of a mucoid P. aeruginosa infection may be readily determined. Analysis may result in therapeutic intervention on the patient being taken.

Thus, in the case of nitrate salts, nitrite salts or NO precursor compounds detection of isotopically labeled nitrogen-15 or oxygen-17/18 in nitric oxide, $N_2O$ or $N_2$ gas in the exhaled breath of the subject after a suitable period of time after administration (depending upon the route of administration) can provide diagnostic information about the existence of P. aeruginosa in the subject's lungs (or other tissues). In the case of urea, isotopically labeled carbon-13, nitrogen 15 or oxygen 17/18 in carbon dioxide or ammonia, or both cleavage products, measured in the exhaled breath of the patient or subject, after a suitable time period has elapsed, can also provide diagnostic information about the existence of P. aeruginosa infection in the subject's lungs (or other tissues). In the case of glycine, isotopically labeled carbon-13 or nitrogen-15 in HCN measured in the exhaled breath of the patient or subject, after a suitable time period has elapsed, can provide diagnostic information about the existence of a mucoid P. aeruginosa infection in the lungs of the patient or subject. In each instance, the isotopically labeled cleavage products are compared with a baseline value obtained for the patient prior to administration of the active compounds.

In a preferred embodiment, isotopically labeled urea and glycine and optionally, at least one additional compound selected from the group consisting of a nitrate salt, a nitrite salt and a NO precursor compound are administered to the subject to be tested for P. aeruginosa infection and, depending on the existence of cleavage products or their isotopic elements (or their absence) measured in the exhaled breath of the subject to be tested, diagnostic information may be used to determine whether or not there is a P. aeruginosa infection in the lungs (or other tissues) of the subject tested and whether, if there such an infection, whether that infection is a mucoid P. aeruginosa infection. In preferred aspects of the invention, a single breath or several breaths taken at a predetermined time after administration of the isotopically labeled compounds may be used to determine the existence or absence of an active P. aeruginosa infection and optionally, whether or not it is a mucoid infection.

In an alternative aspect of the invention, in order to determine that a P. aeruginosa infection is present in the lungs (or other tissues) of the tested patient, measurements of isotopically labeled cleavage products in the breath of the tested subject are made and the concentration of isotopically labeled elements is compared with concentrations of the naturally occurring nitrogen-14, carbon-12 and/or oxygen-16 atoms in the breath of the tested subject. Thus, in this aspect of the invention, a control or baseline may be established for the patient or subject to be tested. A single breath or a number of breaths taken at a predetermined time based upon the time of administration of the isotopically active compounds to the subject may be used to diagnose the subject. Alternatively, a number of breaths at different times may be used in diagnosis. The ratio of an isotopically labeled element(s) to non-isotopically labeled element(s) may be determined and compared to a predetermined reference or control value (ratio of the same elements) determined from the subject prior to administration of the isotopically labeled compounds. A single measurement obtained from the subject which evidences a ratio above the reference ratio may be evidence of the existence of infection and/or mucoid phenotype. A measurement of approximately the reference ratio will be evidence of that an infection does not exist.

In a preferred embodiment, a combination of an isotopically labeled nitrate, nitrite or NO precursor (labeled with for example, nitrogen 15, oxygen 17 or 18) may be used in combination with an isotopically labeled urea (C-13) and an isotopically labeled glycine (N-15) in pulmonary dosage form. In this aspect of the invention, the active compounds are delivered to the lungs of the CF patient or subject, and the patient's exhaled breaths are collected and analyzed to determine the existence of isotopically labeled elements at levels above baseline (control), such that the metabolism of the active compounds is detected (elevated isotopic elements) and the existence of a P. aeruginosa infection is confirmed. The existence of elevated levels of HCN gas and/or isotopic element from the administered glycine will evidence, along with the other cleavage products that the P. aeruginosa is a mucoid infection.

In alternative embodiments, a number of breaths at different times may be taken from the subject and a graph or curve may be generated showing the ratio of the isotopically labeled element to the naturally occurring elements in the breath of the tested subject as a function of time. A curve showing an increase in the ratio of the isotopically labeled element to non-isotopically labeled element over time (compared to a control with no infection) is evidence of the existence of a P. aeruginosa infection. The concentrations of isotopically labeled elements in the samples are compared to a standard ratio which may be obtained from a control group, or more preferably, from the subject prior to administration of the active compounds to the subject pursuant to the diagnostic test.

A curve may be fitted to the measured concentrations and then analyzed, preferably by determining the rate of rise of the curve, or by the magnitude of the plateau. Such an analysis indicates the level of activity of P. aeruginosa species in the subject, which can be used to diagnose the presence of P. aeruginosa in the lungs (or other tissues) of the subject and the phenotype (non-mucoid or mucoid) of the P. aeruginosa infection.

Preferably at least a majority of the exhaled breaths, and most preferably every exhaled breath at a predetermined time for a predetermined period, is sampled for that period or until the determination of the level of P. aeruginosa activity, if present, has reached a preset accuracy.

A predetermined time period after administration of the isotopically labeled active compound to a subject may be used to provide a highly accurate measure of diagnostic value. This period may be determined by using a sample of control subjects (with and without P. aeruginosa infection) who have been administered isotopically labeled compounds and then measuring isotopically labeled elements in the exhaled breath of the subjects after identified periods of time. The predetermined period of time is that period during which samples of a subject are taken after administration Following the step of administering the isotopically labeled active compounds to the subject orally or by pulmonary administration, after an appropriate time period which allows for delivery of the active compounds to the lung tissue and likely site of infection of P. aeruginosa, if present, the exhaled breath of the subject is analyzed to detect a cleavage product or products, which indicates the presence of P. aeruginosa in the lungs or other tissue of the subject and whether or not the P. aeruginosa is predominantly a mucoid or non-mucoid phenotype. The product or products are detected by analyzing a gas sample of the exhaled breath of the subject with a measuring instrument (or a urine, serum or plasma sample for analyzing nitrite, nitrate, NO, cyanate, thiocyanate, biocarbonate levels from cleavage of the active compounds). Such a gas sample can be obtained in a number of ways including, but not limited to, having the subject exhale or blow into a tube connected to the measuring instrument. A breath collection bag, a glass vial containing a septum or a nasal cannula may be used. The subject breathes directly into the breath collection bag or through the septum into the glass vial. In the case of the nasal cannula, such a cannula includes a section of tubing, usually plastic, with two prongs. Each prong is inserted into a nostril and the cannula is then connected to the measuring instrument. As the subject exhales through the nose, the exhaled air flows through the cannula to the measuring instrument.

The type of measuring instrument used to detect the product or products depends upon the type of label, but the present invention may be adapted rather broadly for virtually any appropriate measuring instrument. Preferably, the instrument is a mass spectrometer gas analyzer, or an infrared laser spectrometer. For example, if a nitrogen-15 or carbon-13

(oxygen-17 or oxygen-18) isotopically-labelled substrate is used, the Nitrogen-15 or carbon-13 (oxygen-17 or oxygen-18) isotopically-labelled cleavage product or products can be detected by using a measuring instrument including, but not limited to a mass spectrometer or a gas analyzer, which is sensitive to the nitrogen-15 or carbon-13 (oxygen-17 or oxygen-18) isotope. In one approach, the ratio of the concentration of carbon-13 or nitrogen-15 (oxygen-17 or oxygen-18) isotopically-labelled cleavage product or products to the concentration of carbon-12 or nitrogen-14 (oxygen-16) cleavage product or products is then determined. Since nitrogen-14 and carbon-12 and oxygen-16 are the more abundant isotopes in nature, nitrogen-14, carbon-12 and oxygen-16 atoms are more abundant in unlabelled molecules which are found in the exhaled breath of a patient or subject. Thus, a higher carbon-13/carbon-12, nitrogen-15/nitrogen14, or oxygen 17-18/oxygen-16 ratio determined indicates a higher concentration of the carbon-13, Nitrogen-15, oxygen-17 or oxygen 18 isotopically-labelled cleavage product or products, which positively indicates the presence of P. aeruginosa in the lungs (or other tissues) of the subject. It is noted that the ratio (isotopically-labeled atom/non-isotopically labeled atom) obtained after administration of isotopically labeled glycine and measurement of the resultant isotopically labeled HCN gas may be used further to determine the existence and extent that P. aeruginosa is phenotypically a mucoid variety.

Preferably, at least one of the cleavage products of glycine is a nitrogen-15 isotopically labeled hydrogen cyanide (HCN) gas and urea is carbon-13 isotopically-labeled carbon dioxide. In the case of nitrates, nitrates and NO precursor compounds, at least one of the cleavage products is an isotopically labeled NO gas, $N_2O$ or $N_2$ gas. In certain instances, it may be advantageous to label active compounds with more than one isotopically labeled element such that the cleavage product would contain more than one isotopically labeled Examples of measuring instruments which can be used with carbon-13 isotopically-labelled carbon dioxide include, but are not limited to, an infrared spectrometer and an isotope ratio mass spectrometer. The infrared spectrometers are well known in the art, and have the advantage of being both rapid and accurate, as well as sensitive. Examples of such infrared spectrometers are disclosed in U.S. Pat. No. 5,063,275, which is incorporated by reference herein.

Alternatively, an analytical assay is described which is based on the use of Nitrogen-15 labeled expired nitric oxide (NO), $N_2O$ or $N_2$ gas or C-13 labeled expired $CO_2$ in the present assay. In this method for example, isotope ratio mass spectroscopy (EMS) is used as a detection method for N-15, C-13 (also O-17 or O-18) which occurs naturally in the expired breath of a subject and this ratio is compared with a ratio generated for the expired breath of a test subject after administration of the isotopically labeled active compound (s). A particularly preferred mass spectromer is a Finnegan Delta Plus XL, which is an isotope ratio mass spectrometer. Non-dispersive infrared spectroscopy (NDIRS) analysis and analysis methods which are well known in the art also may be employed. HCN gas may be detected/measured using a mass spectrometer or laser intrared spectrometer or directly, using a chemically integrating dosimeter as described inter alia in U.S. Pat. No. 4,267,023 or after conversion to $CO_2$ or $N_2$. Alternatively, HCN, $CO_2$, CO, NO, $N_2O$ and $N_2$ may be readily measured using a gas analyzer, such as a Picarro gas analyzer available form Picarro, Inc. Sunnyvale, Calif.

A representative test protocol for the present invention is as follows: isotopically labeled active (nitrate, nitrite, NO, NO precursor, urea and/or glycine, preferably urea and glycine and optionally one of nitrate, nitrate, NO precursor) is administered to a subject or patient to be tested. The administration may be by oral or preferably by pulmonary administration, as described in greater detail herein, using an inhaler or other device adapted to deliver an effective amount (generally, an effective amount within the range of about 0.05 to about 25 mg, about 0.25 to about 10 mg, about 0.5 to about 8 mg, about 0.5 to about 5 mg, about 0.75 to about 3 mg) of isotopically labeled active, preferably isotopically labeled nitrate, nitrite or NO precursor (preferably Nitrogen-15 isotopically labeled nitrite, nitrate, NO or S-nitrosothiol, e.g. S-nitrosoglutathione), urea (preferably carbon-13 isotopically labeled urea) and glycine (preferably a Nitrogen-15 isotopically labeled glycine) to the lungs of the patient or subject. After an appropriate period of fasting and prior to administration of the actives, in certain instances, a number of breaths are taken for the subject at a predetermined time to produce a "control ratio" or baseline ratio of isotopically labeled atom to non-isotopically labeled atom in the breath of the subject to be tested. Alternatively, a control ratio for a predetermined time period may be determined using a control population, rather than the subject of the diagnosis. Just prior to the taking of breath samples for the test, a dose of isotopically labeled active (preferably, a combination of actives as described hereinabove) is administered to the subject to be tested either orally or by a pulmonary, preferably an intratracheal, route. Breath samples from the subject are collected after a predetermined time, with the predetermined time being significantly different for oral administration relative to pulmonary administration of the actives. Ratios of isotopically labeled atoms to non-isotopically labeled atoms are measured/determined from the breath of the subject to be diagnosed and this ratio is then compared to the "control ratio". A measured ratio which is significantly higher than the control ratio is evidence of infection by P. aeruginosa, and evidence of increased cleavage of glycine (by measuring cleavage products directly or indirectly) indicates that a P. aeruginosa infection is principally phenotypically mucoid. In instances where the measured ratio of isotopically labeled atom to non-isotopically labeled atom after administration of actives is higher than the control ratio, then P. aeruginosa infectivity is made out. In instances where cleavage of glycine is evidenced, then the presence of a mucoid variety of P. aeruginosa is diagnosed as being present in the patient's lungs.

Advantages of the test are the following: it is practical, sensitive and specific; the validity of the test is not influenced by stress, exercise, hormone imbalances, or some drugs and medications it is a non-invasive method; it is simple to perform and can be readily used in physicians' offices or medical laboratories; it is safe since carbon-13, nitrogen-15, and oxygen-17 and -18 are naturally occurring isotopes found in all carbon-containing and nitrogen-containing substances; it involves no radioactivity, and may be used in children and women.

The carbon-13/Nitrogen-15 test is safe, reliable, and specific in diagnosis of P. aeruginosa, measurement of the severity and type (mucoid/non-mucoid) of P. aeruginosa infections in patients. The invention is also preferred to monitor P. aeruginosa in CF patients, especially those who are being treated with antibiotics. A preferred embodiment of the invention is a kit containing the necessary material for performing the described method. This kit may contain but is not limited to a source of nitrogen-15, carbon-13, oxygen-17 and/or oxygen-18 isotopically labeled actives, preferably in combination, as an oral or pulmonary dosage form; and a breath collection device. The kit may also contain a set of patient instructions for its use. In another embodiment, the kit may additionally contain a blood collection device such as a lancet or hypodermic needle and vacutainer or a urine collection vial or other container for the additional determination of blood (serum or plasma) or urine levels of nitrite and/or nitrate.

Alternatively, at least one of the cleavage products is nitrogen-15 isotopically-labeled nitric oxide, $N_2O$ or $N_2$ (from nitrate, nitrite or NO precursor compound), one is carbon-13 isotopically labeled carbon dioxide (from urea), and one is a carbon-13 and/or a nitrogen-15 isotopically labeled HCN (or $CO_2$ or $N_2$ from HCN). In the case of urea, both carbon-13 isotopically-labelled carbon dioxide and nitrogen-15 isotopically-labelled ammonia could be present as cleavage products, providing that the substrate has both labels. Both ammonia and carbon dioxide have the advantage of being molecules which are present in the exhaled breath of the subject.

In certain instances, the administered urea may be labeled with carbon-13, such that the cleavage product is isotopically labeled carbon dioxide ($CO_2$). The isotopically labeled carbon dioxide may be measured directly. Ratios of isotopically labeled carbon-13 to non-isotopically labeled carbon-12 in the sample breaths may be determined and compared to control ratios. In other instances, the urea may be labeled with oxygen 17 or 18, such that the cleavage product is isotopically labeled carbon dioxide ($CO_2$). The isotopically labeled carbon dioxide may be measured directly and ratios of isotopically labeled oxygen-17 or 18 to non-isotopically labeled oxygen 16 in the sample breaths may be determined and compared to a control ratio. The ratio of $^{13}CO_2$ to $^{12}$CO2 in the $CO_2$ produced from urease within the bacterium and then exhaled can be examined directly by mass spectrometry or laser spectroscopy.

Although a number of instruments may be used to measure cleavage products in the present invention, certain characteristics of the measuring device are important. For example, the measuring instrument used to detect the cleavage product or products should have a number of characteristics. The measuring instrument should be able to measure the concentration of the product or products extremely rapidly. Furthermore, either the measuring instrument itself, or an associated device, should be able to perform the associated analysis, including providing a readout or in the case where a curve is to be generated, generating the curve and fitting the curve and providing the analysis of the curve. Such analyses must be performed rapidly. Preferably, the measuring instrument, alone or in conjunction with the associated device, should be able to measure the concentration and perform the associated analysis within about 10 seconds, and most preferably within about 3 seconds, particularly if substantially every exhaled breath of the subject is to be analyzed.

The term "predetermined time", "predetermined period" or "predetermined time period" (all of which may be used interchangeably within the context of their use in describing the present invention) is used to describe a previously determined (using a control group) period of time or periods of time at which exhaled breaths (or urine, whole blood, serum or plasma samples) are collected from a subject after administration of active compounds in order to analyze for cleavage products to determine whether or not the subject has active P. aeruginosa. In the case of active compounds which has been administered using pulmonary administration, the predetermined time (period of time collecting exhaled breaths from a subject) may be a about 15 second to about 10 minutes, about 30 second to 5 minutes, about 45 seconds to 4 minutes, about one minute to 3 minutes, said time period being initiated any time from about 30 seconds to about an hour, about 1 minute to about 30 minutes, about 2 minutes to about 15 minutes about 3 minutes to about 10 minutes, about 4 minutes to about 7 minutes after pulmonary administration of active compound(s). In the case of oral administration, the predetermined time period for collecting exhaled breaths from a subject may be initiated from about 5 minutes to about 5 hours after administration, about 10 minutes to about 2 hour, about 15 minutes to about 1 hour, about 15 minutes to about 1 hour, about 20 minutes to about 45 minutes, about 25 minutes to about 35 minutes after administration.

After oral or pulmonary administration, isotopically labeled cleavage products such as nitrites, nitrates, NO species, bicarbonate (urea), cyanate and thiocyanate (glycine) from active cleavage may be analyzed from urine, serum or plasma samples.

Thus, the predetermined time period refers to the length of a time period at a particular time (generally after an event, especially the administration of active) required for a cleavage product or products to form and to be exhaled in the breath (or found in the urine, serum or plasma) of the subject. Thus, a number of events must occur. First, the administered active (s) must be accessible to P. aeruginosa in the lungs. Then, the administered active(s) must be cleaved by the enzymes of P. aeruginosa, if present, to form a cleavage product or products. The cleavage product or products must be exhaled in the breath of the subject. Finally, the presence of the cleavage product or products must be detected in the exhaled breath.

Furthermore, the predetermined time period should be such that enough breaths are taken to determine a ratio of isotopically labeled elements to non-isotopically labeled elements in the exhaled the breaths from the subject. These may be compared to a control ratio (from the subject or a control group, as otherwise described herein) from which a diagnosis of P. aeruginosa infection or mucoid P. aeruginosa infection is made. In other embodiments there may be more than one time period such that a series of measurements are made and form the basis for the curve of measured concentrations. In this aspect which relies on multiple measurements (time periods) the concentration will rise rapidly initially so that the fitted curve is substantially linear, and will then plateau after about 10-30 minutes, as the process of formation and exhalation of cleavage product or products reaches a steady state. Eventually, as the administered active is cleaved, the concentration of cleavage product and isotopically labeled element will decrease. The analysis is preferably performed before the curve of measured values reaches a plateau.

The term "control ratio" signifies the ratio of isotopically labeled element to non-isotopically labeled element in a sample obtained from the subject prior to administration of active(s) and/or urea or a similar ratio obtained from a control population, rather than the subject.

This fitting and analysis of a curve of measured concentrations may be preferred over other approaches. However, the method of the present invention allows repeated breath samples to be rapidly obtained either within a single time period or multiple time periods and then maximizes both the speed and the accuracy of analysis by providing a one point reference number (for the single time period analysis) above which diagnosis of active infection may be made or in the case of multiple time periods, fitting the measured values to a curve and then calculating the rate of increase of the curve, which evidences the infection and its intensity.

Any method for identifying the concentration of isotopically labeled nitric oxide, $N_2O$ or $N_2$ (from nitrate, nitrate, NO denitrification), carbon dioxide and/or ammonia (from cleavage of urea) gas or HCN gas (from cyanide synthase) can be used to determine the existence (or absence) and phenotype (mucoid or non-mucoid) of P. aeruginosa in the lungs (or other tissues) of a patient or subject. The measurement of isotopically labeled gas as a cleavage product by action of P. aeruginosa on the actives is evidence of the existence (or absence) of P. aeruginosa in the lungs (and other tissues) of the subject or the existence (or absence) of a mucoid/non-mucoid strain of M. tuberculosis in the lungs (or other tissues) of the subject. Thus, where both isotopically labeled glycine and urea or other active are administered to a subject to be diagnosed, evidence of cleavage of none of the actives is strong evidence of the subject being P. aeruginosa free, evidence of cleavage of urea or other actives but not glycine indicates the existence of a P. aeruginosa infection which is non-mucoid.

In the present invention it is preferred to determine a ratio of an isotopically labeled element (carbon, nitrogen, oxygen) to a non-isotopically labeled element in a cleavage product (gas) being analyzed. For example, if nitric oxide (NO), $N_2O$ or $N_2$ is being measured as a cleavage product pursuant to administration of nitrate, nitrite or NO precursor, a ratio of nitrogen-15 to nitrogen-14 in the breath of a subject is determined. This may be determined readily using mass spectroscopy or infrared laser spectroscopy. In preferred aspects of the invention, a ratio of Nitrogen-15 to Nitrogen-14 in gasses exhaled by a subject to be diagnosed before administration of actives is determined as a baseline ratio. This ratio is generally below 1%

Specifically, an exemplary method of analysis involves the following steps. A plurality of samples of exhaled breath of the subject is collected rapidly, on the order of one sample about every few seconds or so, preferably such that at least a majority, and most preferably substantially all of the exhaled breaths of the subject at a predetermined time for a predetermined period(s) are sampled. Next, the concentration of a cleavage product is measured and the concentration of an isotopically labeled element, such as nitrogen-15, carbon-13, oxygen-17 or oxygen-17 is compared with its naturally occurring counterpart (e.g. respectively, nitrogen-14, carbon-12 and oxygen-16) in the breath of the subject. Where the ratio of isotopically-labeled element to naturally occurring element is approximately 0 or approximately a control ratio (the control ratio is based upon measurements taken in the subject prior to administration of actives), then P. aeruginosa is not present. In cases where the ratio of isotopically-labeled element to naturally occurring element is above a predetermined value (e.g. established from control groups) measurements above the predetermined value and/or increases of the ratio as a function of time, evidences the existence of P. aeruginosa. Where the ratio of isotopically-labeled element or the direct measurement of HCN evidences the cleavage of glycine by cyanide synthase, then a mucoid P. aeruginosa infection is diagnosed.

Although measuring and analyzing exhaled breaths from a subject for a single predetermined period represents a preferred approach to determining the existence or absence of a P. aeruginosa infection, alternative approaches also may be used. In instances where a number of measurements of exhaled breath from the subject are taken from different periods, a curve may be fitted or generated from the measured concentrations. A curve may be fitted to the measured concentrations. If the ratio remains flat at the x-axis (essentially 0 or close to 0-based upon the subject or a control group) as a function of time, the presence of P. aeruginosa is ruled out. The rate of rise of the curve may be determined by calculating the integral or by derivation (calculation of the derivative), preferably after the measurement of the concentration of cleavage product(s) in each sample. The analysis of the curve indicates the level of P. aeruginosa activity in the lungs of the subject. A rapid rise in the measured concentrations (a steeper curve), would evidence a high level of P. aeruginosa activity in the subject, whereas a slower rise in the measured concentrations (a shallower curve) would evidence a lower level of P. aeruginosa activity. If the P. aeruginosa infection is systemic, a greater period of time will be required for absorption and distribution of the labeled compound to the site of infection and release of labeled gasses. The technique will also prove useful in monitoring the responses of the P. aeruginosa infection to drugs, if the drugs are effective then the bacterial load (measured as either the rate of labeled gas increase, or the value of the plateau, will continue to decrease—if the drugs are ineffective due to resistance, then this will not happen and so alternative drug therapies will be tried.

In an analogous manner, if isotopically labeled actives (preferably having different elements labeled so that cleavage products of one active will be distinguishable from cleavage products of another active) are used, these can provide evidence of the existence (or absence) of P. aeruginosa and the type of infection (mucoid vs. non-mucoid) which predominates.

The single point (predetermined time period) approach to diagnostic analysis has a number of advantages, the major ones being the ease of use and rapid nature of the diagnosis. This approach also provides a diagnostic method which can be used in a clinic or even a doctor's office. A single calculation may be made by taking a number of exhaled breaths from the patient or subject for the predetermined period and then analyzing for isotope-labeled elements in the sample, providing a ration of isotopically-labeled elements to non-isotopically-labeled elements and comparing that ratio to a predetermined ratio obtained from the subject or from a control group.

In other approaches, the calculation of a derivative from a graph produced from a number of collection samples (from varying time periods) which provides a number of data points has advantages over other methods of analysis, such as the calculation of an integral. First, the calculation of the derivative does not require a reference breath sample to be obtained before active is administered to the subject. Since the derivative represents the rate of increase of the measured concentrations of a cleavage product or products, the starting concentration of that cleavage product or products is unimportant. However, the initial concentration of the cleavage product or products in the reference breath sample is important for the proper calculation of the integral, since such an initial concentration represents a background value which must be subtracted from the measured concentrations after administration of the active.

After the resultant measurement has reached a predetermined level of accuracy, or after a predetermined time period has elapsed, no more samples are collected.

The present method utilizing a breath assay has a number of advantages. First, the exhaled breath of the subject can be analyzed in real time; that is, there is relatively little delay between the time the P. aeruginosa activity takes place, and the time such activity is measured. Second, the samples of exhaled breath are obtained rapidly and are analyzed immediately in a manner which substantially increases the accuracy of the results. Depending on method, one or multiple samples may be obtained. In general, a single sample (from a number of exhaled breaths) represents a convenient method which exhibits ease of use and patient compliance. In contrast, obtaining multiple samples from the subject increases the accuracy of the test. There is also less statistical error since many samples are collected. In addition, in this aspect, since samples are preferably collected until a preset level of accuracy is reached, ambiguous results can be substantially eliminated, preventing the need for repeating the test.

The readout of isotopic ratios can be performed by sensitive gas mass spectrometry analysis, but also laser spectroscopy techniques which may allow for more compact and portable devices. In certain aspects of the invention, especially where a ratio of isotopically labeled element to non-isotopically labeled element in a gas is to be used in the analysis, a Finnegan Delta Plus XL™ Mass Spectromer may be used. Collection of exhaled gases (which include gaseous cleavage products) from the subject when the cleaved products are gases may be effected using a standard gas collection bag, using a glass vial with a septum (the subject simply blows into the vial through the septum, or using any other method for collecting breaths from the subject. It is also noted that isotopically labeled Nitrogen-15 present in nitrites, NO, nitrates, cyanates and thiocyates in the urine, serum or plasma of the subject from cleavage/reduction of isotopically labeled nitrates, nitrites, NO precursor compounds (denitrification pathway), or glycine (cyanide synthase) may also be analyzed according to the present invention. A ratio of isotopically labeled Nitrogen-15 to non-isotopically labeled Nitrogen in the urine, whole blood, serum or plasma sample after the administration of the isotopically labeled active compound may be determined and compared to control levels taken from urine, whole blood, serum or plasma of the subject prior to labeled active administration. Alternatively, a control group can be used to establish control levels of isotopically labeled nitrites, nitrates, NO, cyanates and thiocyanates in urine, serum or plasma levels and appropriate ratios for comparison purposes. In like fashion, isotopically labeled (carbon-13) $CO_2$ as dissolved carbonate/bicarbonate in the urine, whole blood, serum or plasma also may be analyzed from the cleavage of isotopically labeled (carbon-13) urea (urease) by P. aeruginosa.

In the present method, isotopically labeled active compounds may be administered by oral or preferably, by a pulmonary (e.g. intratracheal) route of administration. In the case of oral administration, the isotopically labeled actives, either alone or in combination are administered orally to a subject to be tested for evidence of P. aeruginosa infection. The isotopically labeled active compounds may be administered in standard oral dosage form, preferably as an immediate release dosage form or as an enteric dosage form (especially when administered in combination with urea), in combination with a pharmaceutically acceptable carrier, additive or excipient. Oral formulations which include urea may be formulated in enteric dosage form to promote release in the small intestine (duodenum, jejunum, ileum) or in combination with a urease inhibitor to inhibit the action of H. pyrlori urease on administered urea prior to its such as acetohydroxamic acid (Lithostat), a bismuth salt such as bismuth nitrate, bismuth carbonate, bismuth salicylate or bismuth citrate, a proton pump inhibitor such omeprazole (Prilosec), esomeprazole (Nexium), lansoprazole (Prevacid), pantoprazole (Protonix) and rabeprazole sodium (Aciphex), or a natural product extract from ranunculus repens, to avoid any action by urease from H. pylori in the gastrointestinal tract, more specifically, the stomach.

Thus, the present invention also relates to pharmaceutical compositions in oral dosage form comprising effective amounts of isotopically labeled glycine, urea, at least one compound selected from the group consisting of a nitrate salt, a nitrite salt, a NO precursor (e.g. S-nitrosothiol compound such as an alkylthionitrile, S-glutathione, S-nitroso-N-acetylpenicillamine) or their pharmaceutically acceptable salts thereof and a urease inhibitor (not isotopically labeled), optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, the isotopically labeled active compounds are administered to the lungs of the subject via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical composition of the invention is used in the form of a powder, the mean particle diameter of the powder is not especially limited but, in view of the residence of the particles in the lungs, is preferably that the particles fall within the range of about 0.1 to 20 μm, and particularly about 1 to 5 μm. Although the particle size distribution of the powder pharmaceutical composition of the invention is not particularly limited, it is preferable that particles having a size of about 25 μm or more account for not more than about 5% of the particles, and preferably, 1% or less to maximize delivery into the lungs of the subject.

The pharmaceutical composition in the form of a powder of the invention can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the isotopically labeled active compounds or mixtures thereof and excipients which provide for immediate release in pulmonary tissue and microparticulating the dried product. Stated more specifically, after dissolving (or dispersing) a pharmaceutically acceptable carrier, additive or excipient in an aqueous medium, glycine, urea, or mixtures of glycine and urea, and optionally at least one compound selected from the group consisting of a nitrate salt, a nitrite salt or a NO precursor compound (S-nitrosothiol compound, e.g., an alkylthionitrile, S-glutathione, S-nitroso-N-acetylpenicillamine), or their pharmaceutically acceptable salts, all isotopically labeled, in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like water-miscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing glycine, urea or mixtures thereof and optionally at least one compound selected from the group consisting of a nitrate salt, a nitrite salt or a NO precursor compound (S-nitrosothiol compound, e.g., an alkylthionitrile, S-glutathione, S-nitroso-N-acetylpenicillamine) and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isotopically labeled active(s) that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., Nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled isoniazid, isotopically labeled urea or mixtures thereof. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of isoniazid and/or urea which is included in the final composition.

The pharmaceutical compositions of the invention are safe and effective for use in the diagnostic methods according to the present invention. Although the dosage of the composition of the invention may vary depending on the type of active substance administered (isoniazid, urea or mixtures thereof) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient can be given to a human adult in a dose of about 0.001 to about 100 mg, about 0.01 mg to about 25 mg, about 0.05 mg to about 15 mg, about 0.1 mg to about 10 mg, about 0.5 mg to about 5 mg, about 1 to about 3 mg, and given in a single dose The form of the pharmaceutical composition of the invention such as a powder, solution, suspension etc. may be suitably selected according to the type of substance to be administered and the action of a target enzyme on the isotopically labeled active compound(s).

As an administration route, direct inhalation via the mouth using an inhaler is usually preferable. Since the pharmaceutical composition of the invention allows direct local administration into the airways and in particular, directly to pulmonary tissue, the active substance contained therein produces immediate effects. Furthermore, the composition is formulated as an immediate release product so that cleavage and analysis can begin soon after administration.

ADVANTAGES

The present invention allows diagnosis of a P. aeruginosa infection in a CF patient or subject, including a mucoid P. aeruginosa infection in a simple diagnostic test, including a breath test. The diagnosis is rapid and effective and displays a number of ancillary advantages as well.

The present invention also always the monitoring of a P. aeruginosa infection in the lungs of a CF patient, during therapy to determine the impact that an antibiotic regimen is having on resolving the infection.

The present invention represents a rapid, one-stop, easily administered test. The present approach of obtaining a sample from the lungs of the CF patient and processing the sample to determine the existence of a P. aeruginosa infection is laborious, time consuming and not cost effective. The present approach creates logistical issues. The present diagnostic test would be administered 'all in one go' obviating the need for precise recall and would reduce/remove laboratory error/chain of custody concerns. The present system allow faster treatment of infected and potentially infectious patients. Finally, administration of a tracer tablet and collecting breath or urine afterwards needs lower level medical skills, making widespread testing by paramedics possible. Samples can easily be mailed to central facilities.

Allows Rapid Detection of Mucoid formation of P. aeruginosa. This is potentially quite harmful to the CF patient and the present method not only can identify mucoid P. aeruginosa infections with great accuracy, but can monitor the progression of a non-mucoid P. aeruginosa infection so that steps can be taken to modify a therapeutic regiment for a more successful outcome.

The following examples provide insight into the use of the present invention. The examples are simply that, exemplary, and are not to be construed to limit the present invention in any way.

EXAMPLES

Administration of Diagnostic Test for Presence of P. aeruginosa Infection

There are a Number of Potential Embodiments of the Diagnostic Assay

Example 1

Inhaled Administration of Labeled Tracer

A. A first embodiment is to administer $^{13}$C-urea by inhalation (such as a dry powder inhaler as described above) in an amount of 0.1 to 10 mg, and the ratio of $^{13}CO_2$ to $^{12}CO_2$ in exhaled breath sample 1 to 60 minutes afterwards (to allow for conversion) is determined by mass spectrometry or laser spectroscopy. The ratio of $^{13}CO_2$ to $^{12}CO_2$ is compared to that of a breath sample obtained before compound inhalation, and an increase in this ratio is indicative of P. aeruginosa infection.

B. A second embodiment relates to replace the use of urea with the use of $^{15}N$-glycine as in the example A above, with analysis of the amount of HCN (labeled with $^{15}N$) compared to HCN in a sample prior to glycine administration in an exhaled breath sample 1 to 60 minutes after administration is determined by mass spectrometry or laser spectroscopy. The ratio of $^{15}N$ to $^{14}N$ is compared to that of a breath sample obtained before glycine inhalation, and an increase in this ratio is indicative of P. aeruginosa infection which is predominantly mucoid.

C. Another embodiment is to administer both $^{13}C$-urea and $^{15}N$-glycine and independently analyse the ratio of $^{13}CO2$ to $^{12}CO_2$ and of $^{15}N$ to $^{14}N$ in exhaled breath sample 1 to 60 minutes after is determined by mass spectrometry or laser spectroscopy. The ratio of $^{13}CO_2$ to $^{12}CO_2$ (from urea) and $^{15}N$ to $^{14}N$ (from glycine) is compared to that of a breath sample obtained before compound inhalation, and so determination of mycobacterial disease and predominance of mucoid phenotype can be simultaneously determined.

D. If desired, isotopically labeled $^{15}N$-nitrate, nitrite salts or NO precursor compounds may be administered to the CF patient, optionally in combination with isotopically labeled urea and/or glycine and the resultant analysis of isotopically labeled metabolites performed. Elevated levels of isotopically labeled metabolites may evidence the presence of a P. aeruginosa infection, and in particular, an infection having a mucoid phenotype.

E. If desired, as described hereinabove, other active compounds and analytes may be measured, such as isotopically labeled $N_2O$, NO or $N_2$ gases, or nitrites, nitrates, NO, bicarbonate/carbonate, cyanate, thiocynate in a blood sample (serum, plasma), or a urine sample.

Example 2

Oral Administration of Labeled Tracer

1) Oral Administration of Labeled Tracer

A.) One approach is to administer $^{13}C$-urea by in an oral dosage in an amount of about 0.1 to 100 mg, and the ratio of $^{13}CO_2$ to $^{12}CO_2$ in exhaled breath sample 1 to 180 minutes (also within the range of about 15-30 minutes to 60 minutes) after administration is determined by mass spectrometry or laser spectroscopy. The ratio of $^{13}CO_2$ to $^{12}CO_2$ is compared to that of a breath sample obtained before compound administration, and an increase in this ratio is indicative of P. aeruginosa infection. It may be desirable to preclude the potential for H. pylori interference with this assay by either enterically coating the urea capsule/tablet so that labeled urea does not come into contact with H. pylori and/or administration of known inhibitors of H. pylori urease such as bismuth salts, as otherwise described herein.

B) Another approach is to replace use of urea with the use of $^{15}N$-glycine with analysis of the ratio of $^{15}N$ to $^{14}N$ in exhaled breath sample 1 to 200 minutes after is determined by mass spectrometry or laser spectroscopy and compared to a predetermined ratio of $^{15}N$ to $^{14}N$ in a breath sample obtained from the patient or subject prior to administration of glycine. In addition, the amount of isotopically labeled HCN may be measured directly and compared with HCN in a breath sample obtained before compound administration. An increase in this ratio in both instances is indicative of P. aeruginosa disease that is likely to have a mucoid phenotype.

C) Another is to orally administer both $^{13}C$-urea and $^{15}N$-glycine and independently analyse the ratio of $^{13}CO_2$ to $^{12}CO_2$ (from urea) and of $^{15}N$ to $^{14}N$ (in HCN from glycine) in exhaled breath sample 1 to 120 minutes after is determined by mass spectrometry or laser spectroscopy. A ureas inhibitor is preferably included to limit the possibility of urease in the GI tract of the patient metabolizing the administered urea before it gets to the lungs. Note that isotopically labeled HCN may be measured directly and compared with HCN in the breath of the CF patient prior to glycine administration. The ratio of $^{13}CO2$ to $^{12}CO2$ (from urea) and $^{15}N$ to $^{14}N$ (from glycine) is compared to that of a breath sample obtained before compound administration, and so determination of P. aeruginosa disease and likely predominance of mucoid phenotype are present.

D. If desired, isotopically labeled (nitrogen-15) nitrate, nitrite salts or NO precursor compounds may be administered to the CF patient orally, optionally in combination with isotopically labeled urea (preferably including a urease inhibitor as otherwise described herein) and/or glycine and the resultant analysis of isotopically labeled metabolites performed. Elevated levels of isotopically labeled metabolites may evidence the presence of a P. aeruginosa infection, and in particular, an infection having a mucoid phenotype.

E. If desired, as described hereinabove, other active compounds may be orally administered and analytes may be measured, such as isotopically labeled $N_2O$, NO or $N_2$ gases, or nitrites, nitrates, NO, bicarbonate/carbonate, cyanate, thiocynate in a blood sample (serum, plasma), or a urine sample, and analysis performed.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

REFERENCES

1. Deturk, W. E. The adaptive formation of urease by washed suspensions of Pseudomonas aeruginosa. J Bacteriol 70, 187-91 (1955).
2. Jahns, T. Regulation of urea uptake in Pseudomonas aeruginosa. Antonie Van Leeuwenhoek 62, 173-9 (1992).
3. Karmali, K., Karmali, A., Teixeira, A. & Curto, M. J. The use of Fourier transform infrared spectroscopy to assay for urease from Pseudomonas aeruginosa and Canavalia ensiformis. Anal Biochem 331, 115-21 (2004).
4. Sundstrom, J., Jacobson, K., Munck-Wikland, E. & Ringertz, S. Pseudomonas aeruginosa in otitis exteina. A particular variety of the bacteria? Arch Otolaryngol Head Neck Surg 122, 833-6 (1996).
5. Deretic, V. in Persistent Bacterial Infections (ed. Nataro, J. P., Blaser, M. J., Cunningham-Runddles, S.) 305-326 (ASM Press, Washington, D.C., 2000).
6. Goldberg, J. B. & Pier, G. B. The role of the CFTR In susceptibility to Pseudomonas aeruginosa infections in cystic fibrosis. Trends in Microbiology 8, 514-20 (2000).
7. FitzSimmons, S. C. The changing epidemiology of cystic fibrosis. Journal of Pediatrics 122, 1-9 (1993).
8. Govan, J. R. W. & Deretic, V. Microbial pathogenesis in cystic fibrosis: mucoid Pseudomonas aeruginosa and Burkholderia cepacia. Microbiological Reviews 60, 539-574 (1996).
9. Martin, D. W. et al. Mechanism of conversion to mucoidy in Pseudomonas aeruginosa infecting cystic fibrosis patients. Proceedings of the National Academy of Sciences of the United States of America 90, 8377-8381 (1993).
10. Fyfe, J. A. & Govan, J. R. Alginate synthesis in mucoid Pseudomonas aeruginosa: a chromosomal locus involved in control. Journal of General Microbiology 119, 443-50 (1980).
11. McAvoy, M. J. et al. Isolation of mucoid strains of Pseudomonas aeruginosa from non-cystic-fibrosis patients and characterisation of the structure of their secreted alginate. Journal of Medical Microbiology 28, 183-9 (1989).
12. Ramsey, D. M. & Wozr~iaU, D. J. $^{T}$Jndersta.~ding the control of Pseudomonas aeruginosa alginate synthesis and the prospects for management of chronic infections in cystic fibrosis. Molecular Microbiology 56, 309-22 (2005).
13. Pedersen, S. 5., Hoiby, N., Espersen, F. & Koch, C. Role of alginate in infection with mucoid Pseudomonas aeruginosa in cystic fibrosis. Thorax 47, 6-13 (1992).
14. Koch, C. & Hoiby, N. Pathogenesis of cystic fibrosis. Lancet 341, 1065-9 (1993).
15. Pedersen, S. S. Lung infection with alginate-producing, mucoid Pseudomonas aeruginosa in cystic fibrosis. APMIS 100(Suppl. 28), 1-79 (1992).
16. Firoved, A. M., Ornatowski, W. & Deretic, V. Microarray analysis reveals induction of lipoprotein genes in mucoid Pseudomonas aeruginosa: implications for inflammation in cystic fibrosis. Infection & Immunity 72, 5012-8 (2004).
17. Koch, C. Early infection and progression of cystic fibrosis lung disease. Pediatric Pulmonology 34, 232-6 (2002).
18. Bonfield, T. L. et al. Inflammatory cytokines in cystic fibrosis lungs. American Journal of Respiratory & Critical Care Medicine 152, 2111-2118 (1995).
19. Cobb, L. M., Mychaleckyj, J. C., Wozniak, D. J. & Lopez-Boado, Y. S. Pseudomonas aeruginosa flagellin and alginate elicit very distinct gene expression patterns in airway epithelial cells: implications for cystic fibrosis disease. J Immunol 173, 5659-70 (2004).
20. Castric, P. A. Glycine metabolism by Pseudomonas aeruginosa: hydrogen cyanide biosynthesis. J Bacteriol 130, 826-31 (1977).
21. Castric, P. A. Hydrogen cyanide production by Pseudomonas aeruginosa at reduced oxygen levels. Can J Microbiol 29, 1344-9 (1983).
22. Firoved, A. M. & Deretic, V. Microarray analysis of global gene expression in mucoid Pseudomonas aeruginosa. J Bacteriol 185, 1071-81 (2003).
23. Gallagher, L. A. & Manoil, C. Pseudomonas aeruginosa PAO1 kills Caenorhabditis elegans by cyanide poisoning. J Bacteriol 183, 6207-14 (2001).
24. Carterson, A. J. et al. The transcriptional regulator AlgR controls cyanide production in Pseudomonas aeruginosa. J Bacteriol 186, 6837-44 (2004).

The invention claimed is:

1. A method for diagnosing a presence of Pseudomonas aeruginosa in the lungs of a subject, including the steps of:

(a) administering an effective amount of at least one isotopically labeled active agent selected from the group consisting of a nitrate salt, a nitrite salt, nitric oxide (NO), a nitric oxide precursor compound, urea and glycine or their pharmaceutically acceptable salts to the subject, said active agent being acted upon by P. aeruginosa to form an isotopically labeled cleavage product or metabolite; and (b) collecting breath, urine, whole blood, plasma or serum samples from the subject; and (c) analyzing said samples to determine a concentration or concentrations of said cleavage product(s) or metabolite(s), said concentration(s) indicating the presence or absence of P. aeruginosa including optionally, a presence or absence of mucoid phenotype P. aeruginosa, in the lungs of said patient.

2. The method according to claim 1 wherein said active agent is selected from the group consisting of sodium nitrate, potassium nitrate, sodium nitrite, potassium nitrite, nitric oxide, a pharmaceutically acceptable S-nitrosothiol compound, urea, glycine, pharmaceutically acceptable salts thereof and mixtures thereof.

3. The method according to claim 2 wherein said S-nitrosothiol compound is an alkylthionitrile.

4. The method according to claim 1 wherein said nitric oxide precursor compound is S-glutathione or S-nitroso-N-acetylpenicillamine.

5. The method according to claim 1 wherein said isotopically labeled active agent is a mixture of urea, glycine or a pharmaceutically acceptable salt thereof, and optionally, at least one compound selected from the group consisting of an isotopically labeled nitrate salt, nitrite salt, nitric oxide and S-nitrosothiol compound.

6. The method according to claim 1 wherein said sample is the breath of said subject taken for a predetermined time.

7. The method according to claim 1 wherein said active agent is isotopically labeled with carbon-13, nitrogen-15, oxygen-17, oxygen-18 or mixtures thereof.

8. The method according to claim 7 wherein said active agent is urea isotopically labeled with carbon-13, nitrogen-15, oxygen-17 or oxygen-18.

9. The method according to claim 8 wherein said urea is isotopically labeled with carbon-13 or nitrogen-15.

10. The method according to claim 1 wherein said active agent is glycine isotopically labeled with nitrogen-15 or carbon-13.

11. The method according to claim 10 wherein said glycine is isotopically labeled with nitrogen-15.

12. The method according to claim 1 wherein said urea is isotopically labeled with carbon-13 and said glycine is isotopically labeled with nitrogen-15.

13. The method according to claim 1 wherein said cleavage product or metabolite is a gas.

14. The method according to claim 13 wherein said gas is $N_2$, $N_2O$, NO, $CO_2$, HCN or mixtures thereof.

15. The method according to claim 14 wherein said gas is a mixture of isotopically labeled $CO_2$, from the action of P. aeruginosa on urea, and HCN, from the action of P. aeruginosa on glycine and optionally, at least one gas selected from the group consisting of $N_2$, $N_2O$ and NO.

16. The method according to claim 13 wherein a measured concentration of said gas is indicative of a P. aeruginosa infection in the lungs of said patient.

17. The method according to claim 14 wherein said gas is HCN or includes HCN and a measured concentration of said HCN gas at a radiometric ratio of at least 1.25 is indicative of a mucoid phenotype of P. aeruginosa in the lungs of said patient.

18. The method according to claim 1 wherein said isotopically labeled cleavage product or metabolite is selected from the group consisting of nitrate, nitrite, dissolved nitric oxide, carbonate/bicarbonate, cyanate, thiocyanate and mixtures thereof, which is measured in the urine, whole blood, serum or plasma of the patient.

19. The method according to claim 18 wherein said cleavage product or metabolite is cyanate, thiocyanate or mixtures thereof or includes cyanate, thiocyanate or mixtures thereof and a measured concentration of said cleavage product or metabolite in a radiometric ratio of at least about 1.25 is indicative of a mucoid phenotype of P. aeruginosa.

20. The method according to any of claims 1-16 wherein said analyzing step comprises comparing at least one ratio of isotopically labeled element(s) to non-isotopically labeled element(s) in said exhaled breath of said subject to a control ratio of isotopically labeled element(s) to non-isotopically labeled elements in the exhaled breath of said subject or a control group prior to administration of said isotopically labeled active agent.

21. The method according to claim 1 wherein said isotopically labeled active agent(s) is delivered to the lungs by pulmonary route of administration.

22. The method according to claim 1 wherein said isotopically labeled active agent(s) is delivered by oral route of administration.

23. The method according to claim 22 wherein said active agent is or includes urea and said active agent is administered by oral route in combination with a urease inhibitor.

24. The method according to claim 22 or wherein said active agent is urea or includes urea and is administered by oral route in an enteric capsule.

25. The method according to claim 1 wherein isotopically labeled glycine and urea are both administered to said subject, alone or in combination with at least one additional isotopically labeled active agent selected from the group consisting of a nitrate salt, a nitrite salt, NO gas and a NO precursor compound, and wherein the absence of glycine cleavage product, urea cleavage and other cleavage products is evidence of the absence of a P. aeruginosa infection in said subject.

26. The method according to claim 1 wherein isotopically labeled glycine and urea are both administered to said subject, alone or in combination with at least one additional isotopically labeled active agent selected from the group consisting of a nitrate salt, a nitrite salt, NO gas and a NO precursor compound, and wherein the absence of glycine cleavage product and the presence of urea cleavage product and optionally, other cleavage products is evidence of a non-mucoid P. aeruginosa infection in said subject.

27. The method according to claim 1 wherein isotopically labeled glycine and urea are both administered to said subject, alone or in combination with at least one additional isotopically labeled active agent selected from the group consisting of a nitrate salt, a nitrite salt, NO gas and a NO precursor compound, and wherein the presence of glycine cleavage product and the presence of urea cleavage product and optionally, other cleavage products is evidence of a mucoid P. aeruginosa infection in said subject.

28. The method according to claim 1 wherein said urea is cleaved to produce carbon dioxide or ammonia.

29. The method according to claim 1 comprising optional steps of fitting the concentrations of said cleavage products obtained to a curve; and analyzing the curve or a plateau of said curve to determine the extent of infection.

*30. A method for diagnosing a urease-positive bacterial infection in the lungs of a subject comprising:*

*administrating to the lungs of the subject, an effective amount isotopically labeled urea;*

*collecting one or more samples of exhaled breath from the subject; and*

*analyzing said samples to determine a concentration of isotopically labeled $CO_2$ in said samples;*

*said concentration indicating the presence or absence of the urease-positive bacterial infection in the lungs of the subject.*

*31. The method of claim 30, wherein the isotopically labeled urea is $^{13}$C-urea.*

*32. The method of claim 30, wherein said samples are taken for a predetermined time.*

*33. The method of claim 30, wherein said gas is $^{13}CO_2$.*

*34. The method of claim 31, wherein the analysis comprises comparing the ratio of $^{13}CO_2$ to $^{12}CO_2$ in said samples to the ratio of $^{13}CO_2$ to $^{12}CO_2$ in a sample obtained from the subject prior to the administration of the isotopically labeled urea.*

*35. The method of claim 31, wherein an increase in the ratio of $^{13}CO_2$ to $^{12}CO_2$ in said samples to the ratio of $^{13}CO_2$ to $^{12}CO_2$ in a sample obtained from the subject prior to the administration of the isotopically labeled urea.*

* * * * *